US009095715B2

(12) United States Patent
Gillberg et al.

(10) Patent No.: US 9,095,715 B2
(45) Date of Patent: *Aug. 4, 2015

(54) IMPLANTED DEVICE DATA TO GUIDE ABLATION THERAPY

(75) Inventors: Jeffrey M. Gillberg, Coon Rapids, MN (US); Mark L. Brown, North Oaks, MN (US); Chris J. Gennaro, Newton, MN (US)

(73) Assignee: Medtronic, Inc., Minneapolis, MN (US)

( * ) Notice: Subject to any disclaimer, the term of this patent is extended or adjusted under 35 U.S.C. 154(b) by 1033 days.

This patent is subject to a terminal disclaimer.

(21) Appl. No.: 13/080,027

(22) Filed: Apr. 5, 2011

(65) Prior Publication Data

US 2012/0165810 A1 Jun. 28, 2012

Related U.S. Application Data

(60) Provisional application No. 61/426,713, filed on Dec. 23, 2010.

(51) Int. Cl.

*A61B 18/14* (2006.01)
*A61N 1/362* (2006.01)

(Continued)

(52) U.S. Cl.

CPC .............. *A61N 1/3621* (2013.01); *A61N 1/371* (2013.01); *A61N 1/3702* (2013.01);

(Continued)

(58) Field of Classification Search

CPC ........... A61B 2018/00351; A61B 2018/00577; A61B 2018/00696; A61B 2018/00839; A61B 2018/00898; A61B 2018/00904; A61B 5/0402; A61B 5/04014; A61B 5/04017; A61B 5/04018; A61B 5/0452; A61B 5/04525; A61B 5/0456; A61B 5/046; A61B 5/0464; A61B 5/0468; A61B 5/0472; A61B 2017/00039; A61B 2017/00044; A61B 2017/0048; A61B 2017/00053

USPC ..................................................... 606/34–52

See application file for complete search history.

(56) References Cited

U.S. PATENT DOCUMENTS 5,271,411 A 12/1993 Ripley
5,411,530 A 5/1995 Akhtar (Continued)

FOREIGN PATENT DOCUMENTS

WO 2004/110258 A2 12/2004
WO 2007095612 A2 8/2007

OTHER PUBLICATIONS

Nitta, T., Scheussler, R.B., Mitsuno, M., Rokkas, C.K., Isobe F., Cronin, C.S., Cox, J.L., Boineau, J.P., (1998) Return Cycle Mapping After Entrainment of VEntricular Tachycardia, Circulation 97:1164-1175.*

(Continued)

*Primary Examiner* — Joseph Stoklosa
*Assistant Examiner* — Eunhwa Kim
(74) *Attorney, Agent, or Firm* — Michael C. Soldner

(57) ABSTRACT

A medical device system and associated method for guiding ablation therapy sense cardiac signals using implantable electrodes and detect spontaneous cardiac events from the sensed cardiac signals. Pacing pulses are delivered in response to detecting a spontaneous cardiac event and a return cycle length is measured. The spontaneous cardiac event is clustered with a previously detected cardiac event in response to the measured return cycle length. Data corresponding to the clustered cardiac events is displayed to guide an ablation therapy.

11 Claims, 7 Drawing Sheets

(51) Int. Cl.
*A61N 1/37* (2006.01)
*A61B 18/00* (2006.01)

(52) U.S. Cl.
CPC ................. *A61B 2018/00351* (2013.01); *A61B 2018/00577* (2013.01); *A61B 2018/00696* (2013.01); *A61B 2018/00839* (2013.01); *A61B 2018/00898* (2013.01); *A61B 2018/00904* (2013.01)

(56) References Cited

U.S. PATENT DOCUMENTS

| | | | | |
|---|---|---|---|---|
| 5,848,972 | A | 12/1998 | Triedman | |
| 6,301,503 | B1 | 10/2001 | Hsu | |
| 6,370,412 | B1 | 4/2002 | Armoundas | |
| 6,400,986 | B1 | 6/2002 | Sun | |
| 6,449,504 | B1 | 9/2002 | Conley | |
| 6,856,830 | B2 | 2/2005 | He | |
| 7,123,954 | B2 | 10/2006 | Narayan | |
| 7,289,843 | B2 | 10/2007 | Beatty | |
| 2003/0028183 | A1* | 2/2003 | Sanchez et al. | 606/34 |
| 2003/0083702 | A1 | 5/2003 | Stadler | |
| 2003/0191404 | A1 | 10/2003 | Klein | |
| 2004/0106956 | A1* | 6/2004 | Sharma et al. | 607/9 |
| 2004/0172067 | A1 | 9/2004 | Saba | |
| 2004/0215273 | A1 | 10/2004 | Van Bolhuis | |
| 2005/0251217 | A1 | 11/2005 | Brown | |
| 2005/0256413 | A1 | 11/2005 | Astrom | |
| 2006/0064020 | A1 | 3/2006 | Burnes | |
| 2006/0224195 | A1 | 10/2006 | Sharma | |
| 2007/0060829 | A1 | 3/2007 | Pappone | |
| 2007/0142736 | A1 | 6/2007 | Cazares | |
| 2007/0219452 | A1 | 9/2007 | Cohen | |
| 2007/0239043 | A1 | 10/2007 | Patel | |
| 2007/0270910 | A1 | 11/2007 | Kornet et al. | |
| 2008/0071182 | A1 | 3/2008 | Cazares | |
| 2008/0125824 | A1 | 5/2008 | Sauer | |
| 2008/0154322 | A1 | 6/2008 | Jackson | |
| 2008/0283771 | A1 | 11/2008 | Li | |
| 2009/0326320 | A1 | 12/2009 | Sinofsky | |
| 2010/0198290 | A1 | 8/2010 | Jackson | |
| 2010/0228309 | A1 | 9/2010 | Belk | |

OTHER PUBLICATIONS (PCT/US2011/065767) PCT Notification of Transmittal of the International Search Report and the Written Opinion of the International Searching Authority.

(PCT/US2011/065772) PCT Notification of Transmittal of the International Search Report and the Written Opinion of the International Searching Authority.

Stevenson, WG. "Catheter Ablation for Ventricular Tachycardia", Circulation, 2007, pp. 2750-2760, vol. 115, American Heart Association, Dallas, TX, USA.

* cited by examiner

IMPLANTED DEVICE DATA TO GUIDE ABLATION THERAPY

RELATED APPLICATION

The present disclosure claims priority and other benefits from U.S. Provisional Patent Application Ser. No. 61/426,713, filed Dec. 23, 2010, entitled "IMPLANTED DEVICE DATA TO GUIDE ABLATION THERAPY", incorporated herein by reference in its entirety.

TECHNICAL FIELD

The disclosure relates generally to implantable medical devices and, in particular, to a medical device system and method for producing data for guiding ablation therapy.

BACKGROUND

Cardiac ablation is a therapy used to treat cardiac arrhythmias. An ablation procedure involves identifying abnormal cardiac tissue from which an arrhythmia is arising or creating a circulating pathway for conduction of the arrhythmia then ablating the cardiac tissue to eliminate a focal point of origin or recirculating pathway. The ablation energy is typically RF ablation though chemical ablation or cyroablation can be used. Ablation therapy is used to treat patients who experience arrhythmias that are refractory to medication, experience serious side effects from medications used to treat arrhythmias, or experience serious or life-threatening arrhythmias.

The clinician has the task of properly identifying a targeted site for ablation that will successfully eliminate the abnormal tissue. The process of identifying an ablation site can include 12-lead ECG studies, electrical mapping using intracardiac electrodes, and may require inducing abnormal rhythms in order to identify and confirm an arrhythmia and an appropriate ablation site. In some cases, the ablation may be incomplete, not entirely eliminating the occurrence of associated arrhythmia episodes. Some patients may experience more than one type of arrhythmia, arising from more than one focal point or reentrant circuit. The procedure for identifying the proper ablation site and the correct number of ablation sites to satisfactorily reduce the occurrence of arrhythmias in a given patient is a challenge to the clinician.

Implantable cardiovertor defibrillators (ICDs) are also used to treat patient's experiencing arrhythmias. ICDs do not eliminate the abnormal tissue causing arrhythmias to occur but can deliver cardiac pacing, anti-tachycardia pacing or cardioversion/defibrillation shocks to prevent or terminate an arrhythmia episode. ICDs typically acquire data relating to an arrhythmia episode when it does occur, including, for example, an intracardiac electrogram (EGM) strip, cardiac cycle lengths measured during the episode, EGM signal morphology data, data relating to the onset of the episode, and therapies delivered to treat an arrhythmia.

Patients receiving ICDs may experience a high occurrence of shock therapies which are painful and can reduce the quality of life of the patient. Ventricular ablation can be used in ICD patients that experience recurrent ventricular tachycardia (VT) or VT storms to reduce the number of shocks required by the ICD. Data stored by an ICD relating to sustained or non-sustained VT can include information useful to a clinician performing ablation procedures. Data stored by an ICD can be uplinked to an external ICD programmer for manual review and analysis by a clinician performing an ablation, however the large amount of episode data can pose considerable data analysis burden on the clinician. What is needed therefore, is a system and method that provides a clinician information acquired by an ICD in a useful format to assist the clinician in efficiently and effectively performing an ablation procedure.

DETAILED DESCRIPTION

Figure 1:
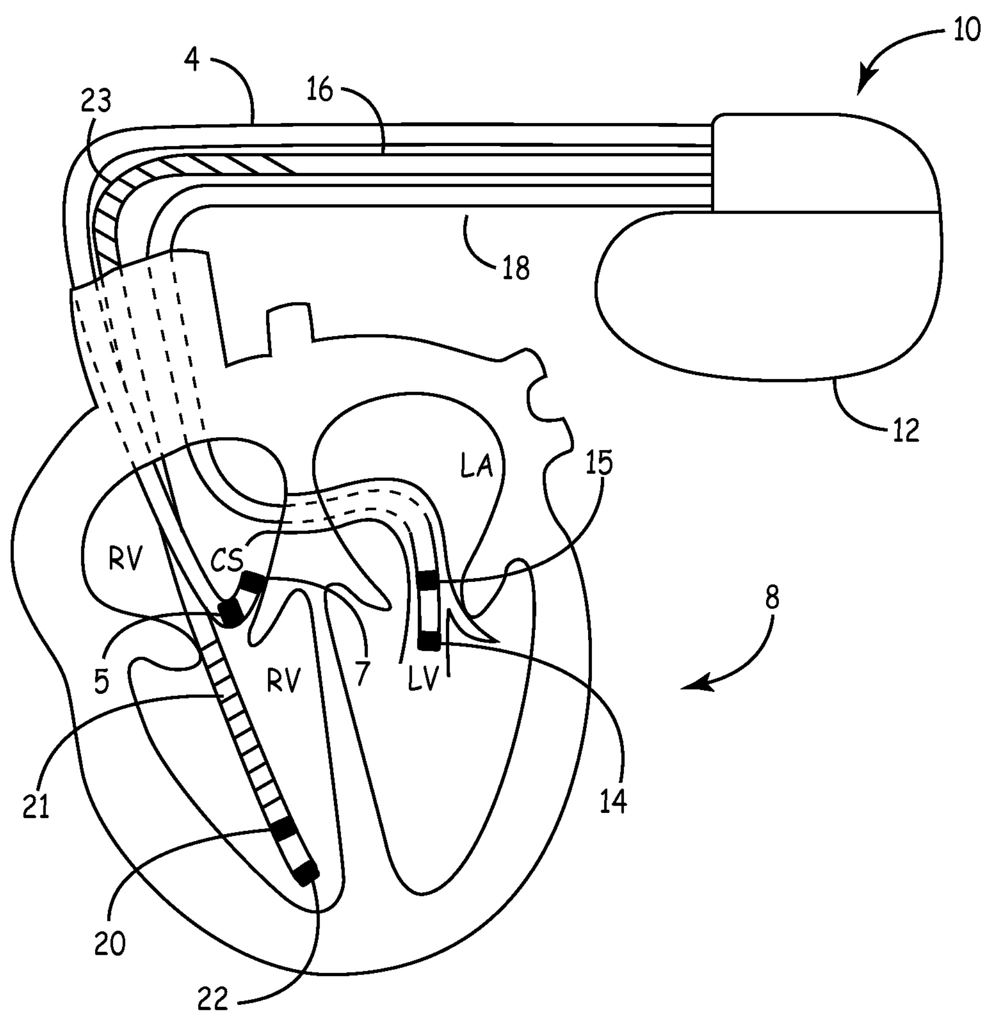
FIG. 1 is a schematic representation of an implantable medical device (IMD).

In the following description, references are made to illustrative embodiments. It is understood that other embodiments may be utilized without departing from the scope of the invention. For purposes of clarity, the same reference numbers are used in the drawings to identify similar elements. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

FIG. 1 is a schematic representation of an implantable medical device (IMD) 10. IMD 10 is embodied as an ICD in FIG. 1. Methods described herein, however, should not be interpreted as being limited to any particular IMD. Instead, embodiments may include any IMD so long as the device utilizes electrodes for monitoring the cardiac rhythm of a patient by sensing cardiac EGM signals, with or without therapy delivery capabilities.

In FIG. 1, the right atrium (RA), left atrium (LA), right ventricle (RV), left ventricle (LV), and the coronary sinus (CS), extending from the opening in the right atrium to form the great cardiac vein, are shown schematically in heart 8. Two transvenous leads 16 and 18 connect IMD 10 with the RV and the LV, respectively. A third transvenous lead 4 is positioned in the RA. Each lead includes at least one electrical conductor and pace/sense electrode. For example, leads 16 and 18 are respectively connected to pace/sense electrodes 20, 22, and 14, 15. RA lead 4 carries pace/sense electrodes 5 and 7. In addition, a housing electrode 12 can be formed as part of the outer surface of the housing of the device 10. The pace/sense electrodes 5, 7, 14, 15, 20, 22 and housing electrode 12 can be selectively employed to provide a number of unipolar and bipolar pace/sense electrode combinations for pacing and sensing functions. The depicted positions in or about the right and left heart chambers are merely illustrative. Moreover, other leads and pace/sense electrodes can be used instead of, or in combination with, any one or more of the depicted leads and electrodes.

The electrodes designated herein as "pace/sense" electrodes may be used for both pacing and sensing functions. In other embodiments, these electrodes can be used exclusively as pace or sense electrodes in programmed or default combinations for sensing cardiac signals and delivering pacing pulses. The leads and electrodes described can be employed to record cardiac signals. The recorded data can be periodically transmitted to a programmer or other external device enabled for telemetric communication with the IMD 10. As will be described in detail below, pace/sense electrodes will be used in collecting data relating to arrhythmia episodes for use in guiding ablation therapy.

An RV coil electrode 21 and a superior vena cava (SVC) coil electrode 23 are also shown as being coupled to a portion of RV lead 16. Coil electrodes can additionally or alternatively be coupled to portions of RA lead 24 or CS lead 18. The coil electrodes 21 and 23, or other similar electrode types, can be electrically coupled to high voltage circuitry for delivering high voltage cardioversion/defibrillation shock pulses and optionally for collecting cardiac electrical data relating to arrhythmia episodes for use in guiding ablation therapy.

Electrodes shown in FIG. 1 can be disposed in a variety of locations in, around, and on the heart and are not limited to the locations shown. Furthermore, other lead and electrode systems may be substituted for the system shown in FIG. 1, including electrodes placed on or around the IMD housing. The system and associated methods described herein may include the use of electrodes for sensing atrial signals and ventricular signals for detecting cardiac arrhythmias and for clustering arrhythmia episodes according to common characteristics. In other embodiments, single chamber, dual chamber or multi-chamber systems may be used which include one or more leads used to position electrodes in, on or around the heart chambers.

Figure 2:
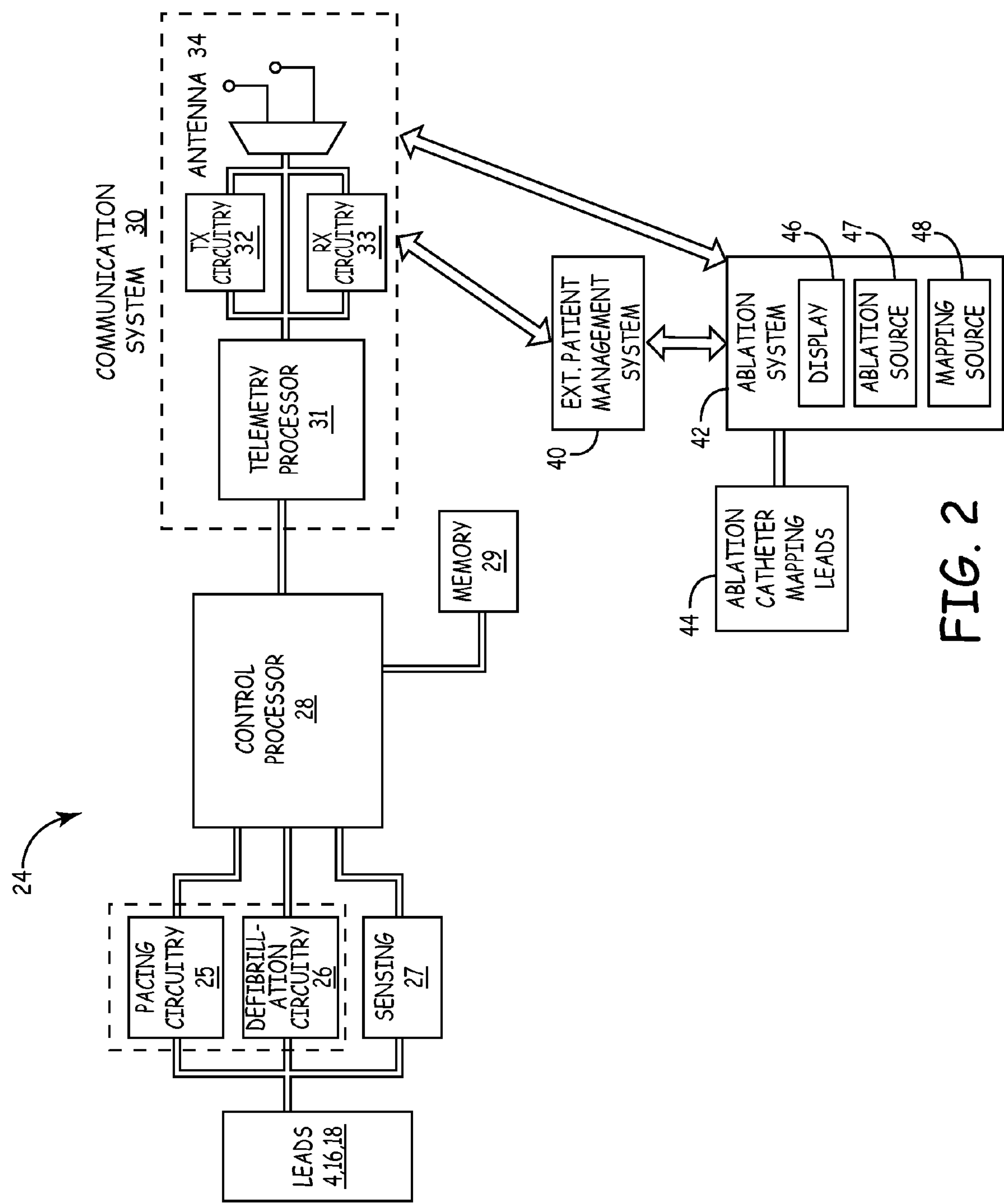
FIG. 2 is a functional block diagram of an ICD system used in combination with an ablation system for guiding ablation therapy.

FIG. 2 is a functional block diagram of an ICD system used in combination with an ablation system for guiding ablation therapy. Circuitry 24, located within IMD 10 of FIG. 1, includes pacing circuitry 25, defibrillation circuitry 26, sensing circuitry 27, control processor 28, memory 29, and communication system 30. Leads 4, 16 and 18 are connected to pacing circuitry 25, defibrillation circuitry 26 and sensing circuitry 27. Each lead (and in turn individual electrodes associated with each lead) coupled to the IMD may be used in multiple capacities to sense cardiac depolarizations (e.g. P-waves and R-waves), deliver pacing pulses including anti-tachycardia pacing (ATP) pulses, and deliver defibrillation or cardioversion shocks.

Control processor 28 receives input through sensing circuitry 27 from leads 4, 16 and 18 concerning depolarizations sensed by the electrodes connected to leads 4, 16 and 18. Based on input received from sensing circuitry 27, control processor 28 performs an arrhythmia detection algorithm for detecting arrhythmias and selecting a therapy as needed. Therapy may include providing ATP therapy pacing electrodes using pacing circuitry 25 and selected pacing electrodes, providing defibrillation or cardioversion shocks using defibrillation circuitry 26 and a selected high voltage electrode, or providing no treatment at all.

Control processor 28 stores selected data to memory 29, and retrieves stored data from memory 29 as necessary. As will be described in detail herein, control processor 28 extracts characteristics from arrhythmia events and stores these characteristics in memory 29. Processor 28 may further cluster or group arrhythmia events based on a correlation between extracted characteristics and store the clustered arrhythmia events in memory 29.

Communication system 30 includes telemetry processor 31, transmission circuitry 32, receiving circuitry 33, and antenna 34. Communication system 30 allows communication between IMD 10 and devices external to the patient. IMD 10 is shown in bi-directional telemetric communication with an external patient management system 40, which in turn is in communication with an ablation system 42. Additionally or alternatively, IMD 10 may be in direct communication with the ablation system 42.

In one embodiment, external patient management system 40 includes a programmer that is used at bedside or in a clinical setting for interrogating IMD 10 to retrieve data stored in memory 29 and for programming operating parameters in IMD 10. External patient management system 40 may include or be embodied as a home monitor that retrieves data from IMD 10 in a patient's home for use in remote patient monitoring. External patient management system 40 may include a communication network linking a programmer or home monitor to a database accessible by a clinician for reviewing retrieved patient data and current IMD operating status. A networked patient management system 40 allows data and information collected by IMD 10 relating to arrhythmias experienced by the patient to be transferred to an ablation system 42.

External patient management system 40 may transmit data to the ablation system 42 for use in guiding an ablation therapy. External patient management system 40 may receive data or instructions from the ablation system to allow cooperative acquisition and interpretation of data between the two systems 40 and 42 for guiding an ablation therapy. Received instructions may include instructions for performing particular diagnostic testing using IMD 10 prior to, during or after an ablation procedure. Alternatively, the ablation system 42 is in direct communication with IMD 10 for retrieving data and/or transferring instructions for guiding an ablation procedure.

Ablation system 42 includes a user display 46, an ablation source 47, and a mapping source 48 which are adapted to be coupled to an ablation catheter and mapping lead(s) 44. The mapping source 48 delivers pacing pulses to mapping electrodes positioned on one or more mapping leads 44 and pace map data is displayed on display 46. Mapping source may also deliver stimulation pulses for inducing tachycardia or fibrillation to allow activation maps to be acquired during an arrhythmia. In other embodiments, the ablation system 42 may include 12-lead ECG sensing for use in identifying the anatomic location of the origin or pathway of a tachycardia.

The ablation source 47 generates ablative energy delivered by the ablation catheter 44 to a targeted ablation site identified using data provided by the IMD and stored in memory 29 relating to arrhythmia episodes experienced by the patient. The IMD 10, external patient management system 40, and ablation system 42 may therefore be configured to function cooperatively to acquire data and information that is displayed in a common image on display 46 to guide the ablation procedure.

Display 46 may be a graphical user interface that allows the clinician to select different screens of information and select actions or functions to be performed by the system. For example, one screen or window may list summary data acquired by the IMD relating to arrhythmia episodes potentially targeted for ablation therapy. Another screen or window may provide an image of the patient's heart, activation map locations and associated EGM/ECG morphology. Registered locations of intracardiac pace/sense electrodes (coupled to the IMD), mapping electrodes, and/or the ablation electrode may be superimposed on a mapping image.

Figure 3:
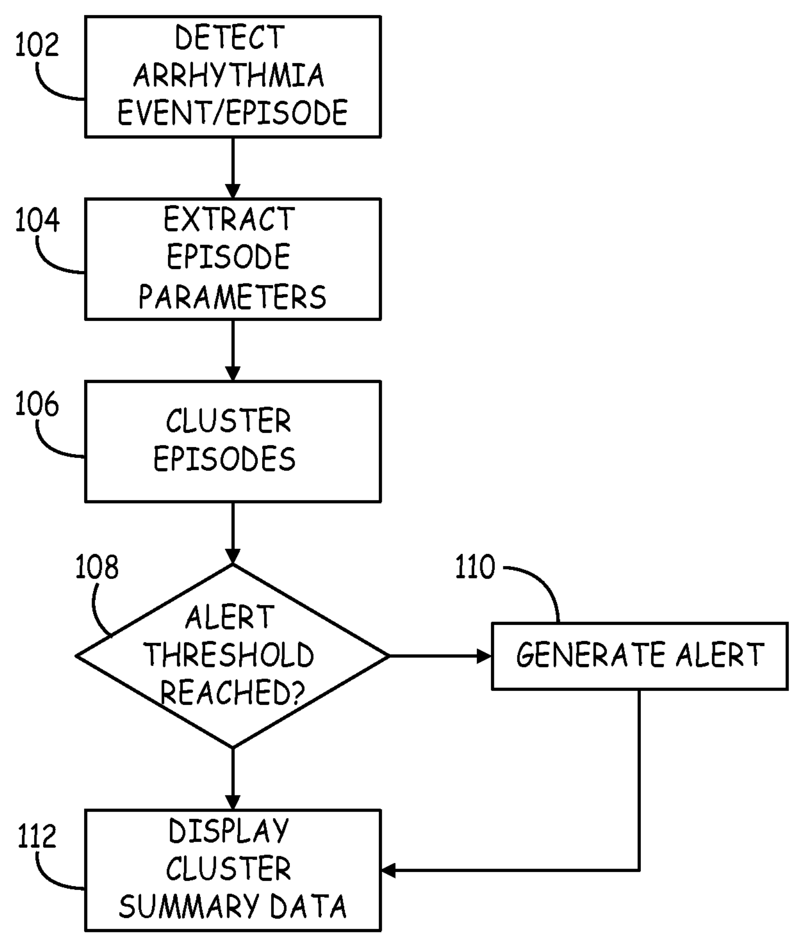
FIG. 3 is a flow chart of a method for acquiring data for guiding an ablation therapy.

FIG. 3 is a flow chart 100 of one method for acquiring data for guiding an ablation therapy. At block 102, an arrhythmia event or episode is detected. Arrhythmia episodes may include all ventricular arrhythmias, atrial arrhythmias, and double tachycardia episodes (occurring in both atrial and ventricular chambers). Events or episodes detected at block 102 may include premature ventricular contractions (PVCs), sustained arrhythmias and non-sustained arrhythmias and may be events that are treated or untreated by the IMD. Events may be triggering events or precursors that precede a tachycardia or fibrillation episode. Triggering events may be a PVC, a non-sustained arrhythmia episode, or other accelerated rhythm.

At block 104, episode parameters are extracted. Episode parameters may include any parameters used to detect the event or episode and may further include parameters extracted after detection for use in characterizing the detected event or episode. Episode parameters may include chamber of origin, mean cycle length, cycle length regularity, representative morphology of the cardiac signal, morphology matching score to a known morphology template, regularity of morphology matching scores relative to a known template or relative to matching successive beats to each other during a tachycardia, measurements relating to the episode onset and/or offset, timing correlation to a reference electrogram (such as a subcutaneous or surface ECG), and A-V sensed event patterns if available. When the detected event is an individual beat, like a PVC, a representative morphology and coupling interval may be stored.

Other sensor signals besides cardiac EGM or subcutaneous ECG signals may also be used for extracting episode parameters. For example if a blood pressure sensor, oxygen sensor, heart wall motion sensor or other sensor providing a signal correlated to patient hemodynamic status is available, a parameter corresponding to hemodynamic stability of the patient during a detected episode may be extracted as an episode parameter.

The episodes are clustered into groups of episodes characterized by similar parameter values at block 106. The clustering operation may be thought of as plotting detecting episodes in a multi-dimensional plot with each dimension representing an episode parameter. Episodes having similar characteristics will appear as clusters in the multi-dimensional plot. In an illustrative example, 50 episodes may be detected in a patient over a period of time. Of those episodes, five episodes may be SVT episodes and the remaining 45 may be VT episodes. Of the 45 VT episodes, three distinct episode types may be identified as a result of the clustering process, e.g. due to differences in morphology, cycle length, onset or other extracted parameters.

A cluster of VT episodes may be further indicated as most likely being a focal VT episode or a reentrant VT based on cycle length, therapy success, EGM morphology regularity or other parameters. For example, a focal VT may be less regular in cycle length and EGM morphology from beat-to-beat and may be more likely to spontaneously terminate. Knowing whether the VT is focal in origin or a reentrant VT will be useful to a clinician in guiding the ablation procedure.

If a particular episode type reaches an alert threshold at block 108, a alert is generated at block 110 to notify a clinician or patient that therapeutic intervention may be warranted. The alert threshold may be programmable and may be defined as a total number of episodes in a single cluster or a group of clusters. The alert threshold may include time dependency such that the frequency of episodes occurring in a particular cluster must increase to reach an alert threshold level. An alert threshold generated by an ICD may indicate that the episode type occurs with such a high degree of frequency that the patient may be a candidate for ablation therapy. The alert threshold may be programmed by the implanting physician, then viewable by a primary physician so that the primary physician understands that an electrophysiological (EP) limit has been reached and a referral back to an EP specialist is warranted.

At block 112, cluster summary data is displayed to a clinician. The process shown in flowchart 100 may be implemented in a distributed manner across an IMD/ablation system. The IMD may detect arrhythmia episodes at block 102 and the episode may be stored by the IMD. Episode parameters and episode clustering may then be performed by an external processor in external patient management system 40 or ablation system 42 using episode data retrieved from the IMD. The cluster summary data may then be displayed to a clinician upon request, by an external patient management system 40 associated with the IMD or by an ablation system 42. Alternatively, the episode detection, parameter extraction, and episode clustering may be performed by the IMD. The episode cluster data may then be transmitted to an external system component 40 or 42 for display to a clinician.

In some embodiments, the episode cluster data, after being uplinked to an external device such as a remote patient management network, may be downloadable in a transferrable electronic data format for email transmission or display on a secure website to be reviewed by a clinical specialist prior to scheduling a clinical consultation.

The displayed information can then be used by the clinician to guide an ablation therapy. For example, the clinician will be aware if the patient is experiencing more than one type of VT episode. The clinician is able to target the most clinically important arrhythmias based on the cluster data provided, e.g. the episode clusters having the shortest cycle length, occurring with greatest frequency, or most hemodynamically unstable.

Flow chart 100 is intended to illustrate the functional operation of the device, and should not be construed as reflective of a specific form of software or hardware necessary to practice the methods described. It is believed that the particular form of software, hardware and/or firmware will be determined primarily by the particular system architecture employed in the device and by the particular detection and therapy delivery methodologies employed by the device. Providing software, hardware, and/or firmware to accomplish the described functionality in the context of any modern IMD and ablation system, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

Figure 4:
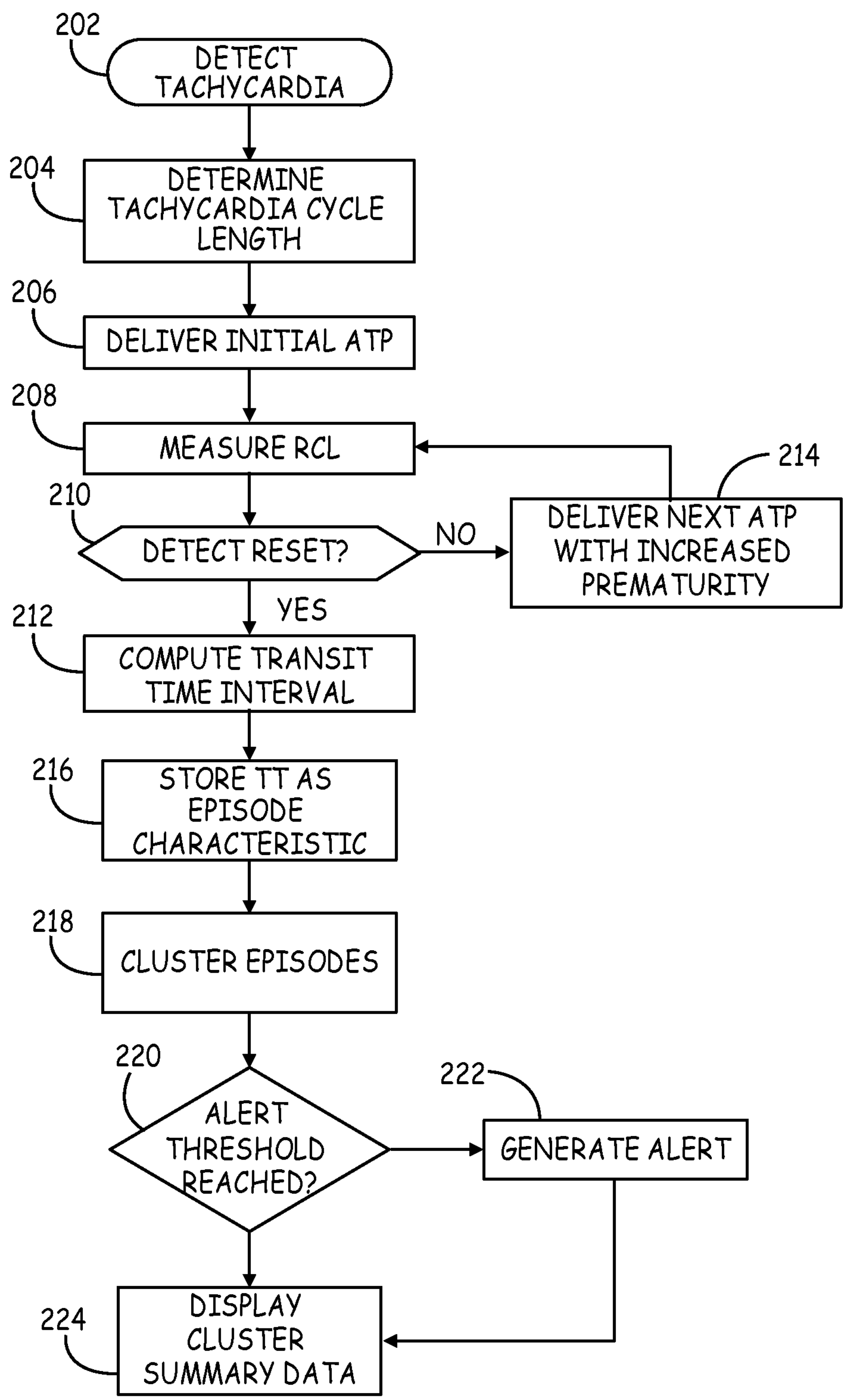
FIG. 4 is a flowchart of another method for providing arrhythmia episode data for guiding ablation therapy.

FIG. 4 is a flowchart 200 of another method for providing arrhythmia episode data for guiding ablation therapy. In this method, a return cycle length (RCL) is measured for use in clustering detected episodes and for guiding a clinician to an ablation site. For details regarding the concepts associated with measuring RCL, reference is made to commonly-assigned U.S. Pat. Publication No. 2010/0198290 (Jackson et al.), hereby incorporated herein by reference in its entirety.

At block 202, a spontaneous tachycardia episode is detected. Tachycardia detection may be performed according to any detection algorithm implemented in the IMD, including rate- and morphology-based algorithms. The episode may be detected using any available sensing electrodes. At block 204, the cycle length of the tachycardia is measured and is stored as an episode characteristic for use in clustering episodes. The tachycardia cycle length (TCL) is further used to determine a pacing cycle length for an ATP regimen such that the ATP pulses are delivered at cycle lengths that are shorter than the TCL.

At block 206, an initial ATP therapy is delivered. The number of pulses and the total prematurity of the initial ATP regimen may be delivered according to any programmed settings, e.g. according to a first level of therapy in a tiered menu of therapies. The "prematurity" of a single ATP pulse is the difference between that pulse's ATP cycle length and the TCL. The total prematurity of the ATP regimen is the sum of all of the ATP pulse prematurities in an ATP sequence. The initial ATP therapy may be a burst, ramp, ramp plus burst or any other ATP regimen.

Following the last pulse of the ATP therapy, the RCL is measured at block 208. The methods generally disclosed in the above-incorporated '290 reference may be used for measuring RCL and computing a transit time as generally discussed below. The RCL is the time between delivery of the last pacing pulse of an ATP sequence and the first sensed event occurring after the last pacing pulse.

At block 210, the RCL is analyzed to determine if reset is detected. When timed appropriately during the TCL, an ATP depolarization wavefront will be injected ahead of a circulating reentrant wavefront of the tachycardia. This phenomenon is referred to as "reset" in that the ATP depolarization has altered a cycle length within the tachycardia circuit. If the injected ATP depolarization is the final pulse of an ATP regimen, the next depolarization sensed at the electrode site will be the injected ATP depolarization after it travels around reentrant circuit and back to the pace/sense electrode. The RCL will be shorter than the expected TCL because the injected ATP depolarization has "jumped in line" ahead of the next expected tachycardia depolarization.

Accordingly, a measured RCL that is less than the sum of the measured TCL and the total prematurity of the ATP sequence is an indication that reset has occurred. Reset is detected at block 210 based on a comparison of the measured RCL to the TCL and total prematurity. If the RCL is approximately equal to (within predetermined uncertainty limits) or greater than the sum of the total prematurity plus the TCL, reset is not detected. Uncertainty limits may take into account a known or unknown variation in the TCL. If reset is not detected, another ATP regimen is delivered at block 214 with a greater total prematurity than the initial ATP regimen.

When reset occurs, i.e. when the RCL is less than the TCL plus the total prematurity of the ATP pulses, the last pulse of the ATP regimen has traveled the distance between the pace electrode and the tachycardia site of origin. The RCL observed after a reset allows a direct measurement of the transit time (TT) which is correlated to the difference between the RCL at which reset occurs and the TCL. The TT is directly correlated to the distance from a pace/sense electrode to the site of origin of the tachycardia. Transit time can be used to discriminate between SVT and VT as well as help to localize a site of tachycardia origin for guiding an ablation therapy.

Once reset is detected, the TT corresponding to the distance between the stimulating electrode and the tachycardia origin is computed at block 212. The TT is stored as an episode characteristic at block 216. When detected episodes are clustered at block 218, after each detected episode, periodically or upon request by a user, the measured TCL, RCL, and TT, or any combination thereof, may be used as episode characteristics during the clustering process.

While not explicitly shown in FIG. 4, it is recognized that a limited number of ATP sequences may be delivered in an attempt to detect reset. If reset is not detected, even after adjusting the total prematurity of the ATP sequence, a minimum distance from the stimulating electrode to the tachycardia site of origin can still be estimated based on the RCL and the maximum total prematurity of the attempted ATP sequences. The distance corresponds to a time that is longer than the sum of the measured RCL and total prematurity. An ATP therapy delivered in order to measure a RCL may or may not terminate the tachycardia.

After assigning an episode to a cluster using the measured TT at block 218, the number of episodes in each cluster can be compared to an alert threshold at block 220. As described above, if an alert threshold is met, an alert is generated at block 220 to notify a clinician or patient that therapeutic intervention may be warranted. At block 224, cluster summary data obtained using RCL measurements is displayed to a clinician upon user request.

Figure 5:
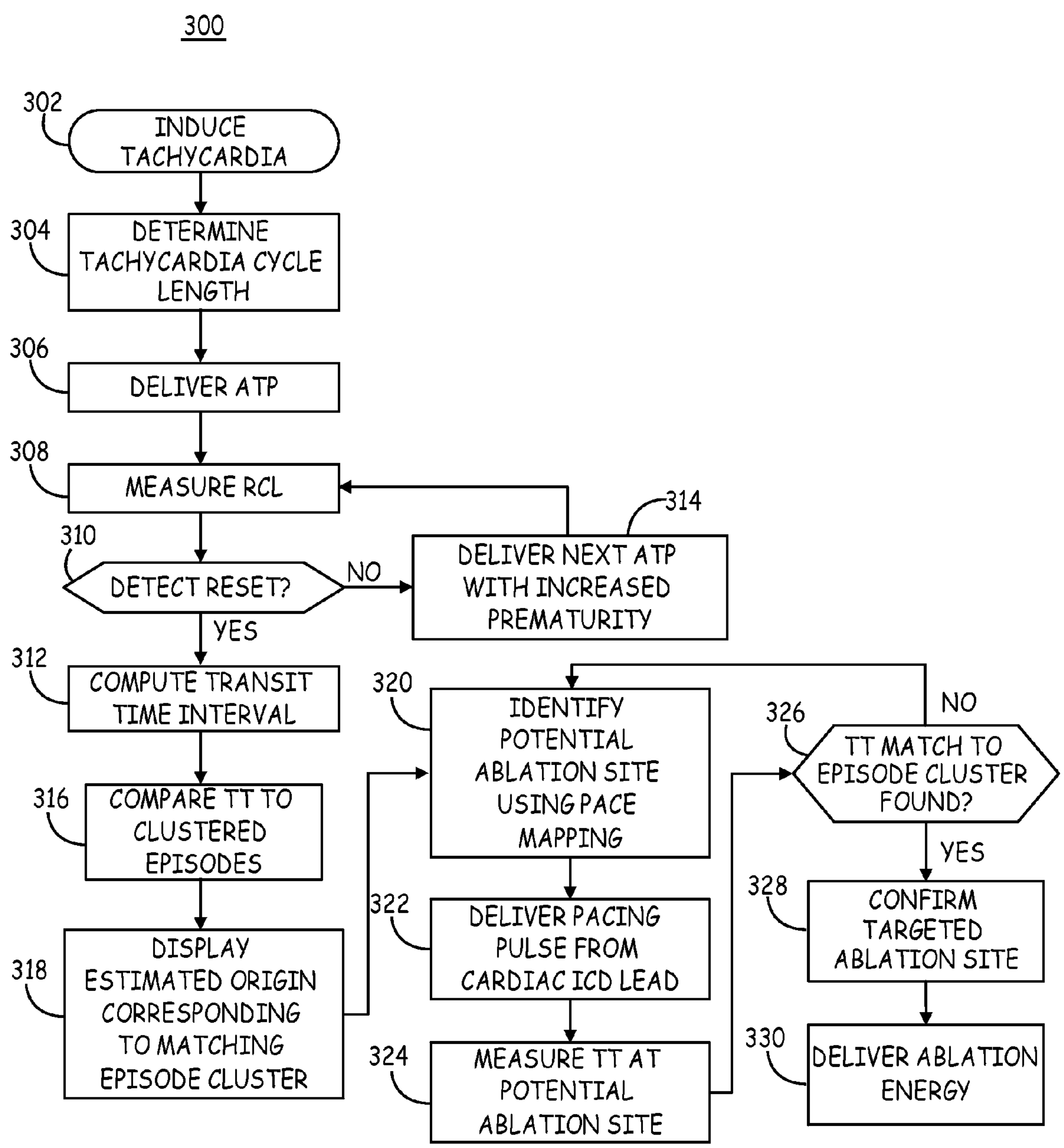
FIG. 5 is a flowchart of a method for identifying a tachycardia site of origin during an ablation procedure.

FIG. 5 is a flowchart 300 of a method for identifying a tachycardia site of origin during an ablation procedure. At block 302, tachycardia is induced. The cycle length of the induced tachycardia is measured at block 304. ATP is delivered at block 306 to allow a RCL to be measured at block 308. The ATP is delivered using the same pace electrode as used for delivering ATP when the patient experiences spontaneous arrhythmias.

The ATP regimen delivered at block 306 may be selected based on a match between the TCL and an episode cluster identified from the IMD data. If there is a match between a TCL of an episode cluster and the induced TCL, the ATP sequence found to reset the episode type may be used at block 306. Alternatively, a default ATP sequence may be delivered. Adjustments to the ATP sequence may be made at block 314 until reset is detected at block 310.

The TT is computed at block 312 using the RCL and the measured TCL. The TT is compared to episode clusters at block 316 to determine if a match is identified. Other episode parameters may also be used such as TCL, morphology parameters or any of those listed previously.

An episode cluster matching the induced TCL and measured TT is identified from episode cluster data retrieved from the IMD at block 318. A display may be generated at block 318 indicating an approximate location of the tachycardia site of origin relative to the stimulating electrode. If the induced VT matches a cluster, the VT is concluded to correspond to a clinical VT experienced by the patient, which may then be targeted for ablation therapy. The site of tachycardia induction and the site of intrinsic tachycardia origin need not be the same to produce the same type of VT. If the VT is hemodynamically stable, mapping can be performed during the VT to identify a location within the VT circuit to target for ablation.

At block 320, a potential ablation site is identified using any technique preferred by the clinician such as pace mapping, ECG morphology analysis, VT entrainment or other method. The ablation catheter is advanced to position an ablation electrode at the potential site.

A pacing pulse is delivered at block 322 using the pace electrode coupled to the IMD and used by the IMD for measuring RCL and TT in generating episode cluster data. Using the ablation electrode at the potential ablation site, the evoked potential is sensed at the potential ablation site in response to the pacing pulse. The transit time for the pacing pulse to travel to the potential ablation site is measured at block 324. If this transit time matches the TT associated with an episode cluster targeted for therapy, as determined at decision block 326, the potential site is confirmed as a targeted ablation site at block 328. Ablation energy is delivered at block 330 to treat the episode type. If the TT does not match an episode cluster TT as determined at block 326, the process returns to block 320. The ablation electrode may be repositioned to a new potential ablation site. Future episode cluster data may be acquired for confirming successful treatment of the episode type. In other words, absence of future episodes matching the data cluster representing the treated episode type would indicate treatment success.

Figure 6:
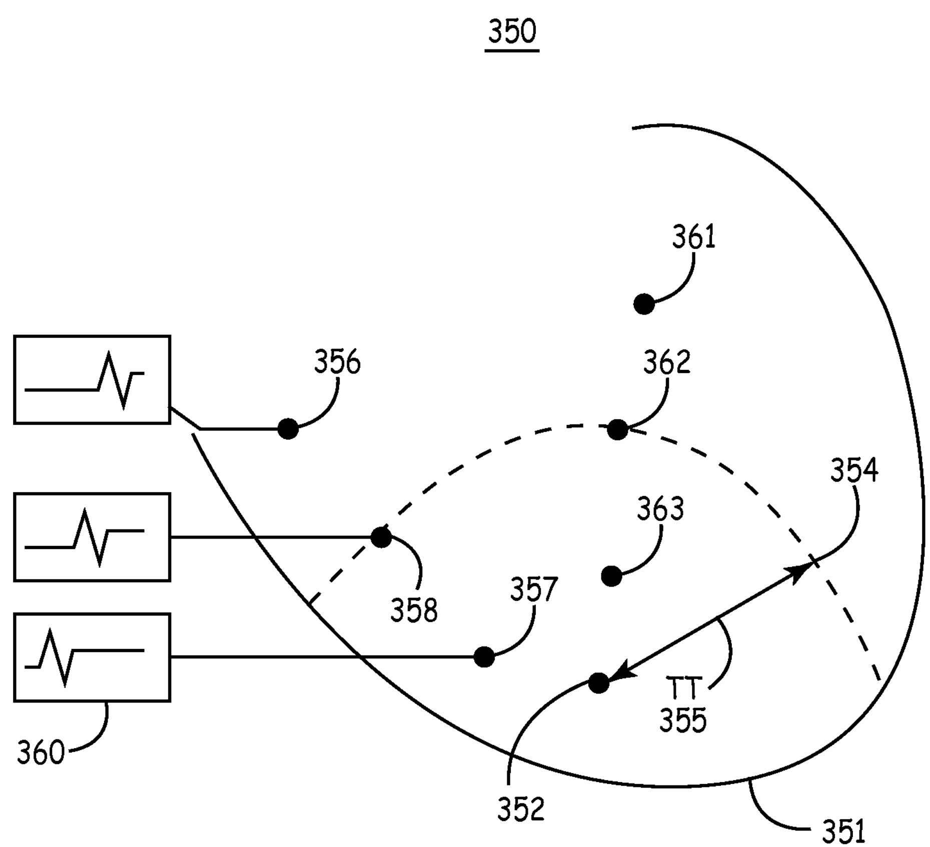
FIG. 6 is a schematic drawing of information included in a clinician display according to one embodiment.

FIG. 6 is a schematic drawing of information included in a display 350 according to one embodiment. Display 350 may be implemented in an ablation system 42 (shown in FIG. 1) incorporating data received from the IMD 10 directly or via external patient management system 40. Once the distance from the pacing electrode to the tachycardia origin is approximately known based on TT, an activation map can be generated during cardiac pacing. On a display 350, the location of the IMD pace electrode 352, typically an RV pace electrode is superimposed on an image of the patient's heart 351 or portion thereof. An ablation site guidance line 354 is displayed marking an approximate distance from the pacing electrode 352 corresponding to the measured TT 355 of an episode cluster. If a transit time is not measured because reset was not detected, a guidance line 354 may mark a boundary indicating a minimum TT (or distance) to the tachycardia circuit based on a RCL at which reset did not occur.

A pacing pulse can be delivered by the IMD pace electrode 352 and an activation map may be generated from a single pacing pulse using, for example, non-contacting imaging systems, such as EnSite 3000, Endocardial Solutions Incorporated, St. Paul, Minn. The activation map is superimposed with the ablation site guidance line 354, with mapping locations 356 through 358 and 361 through 363 indicated by symbols. Corresponding EGM morphologies 360 for the map locations 356-358 and 361-363 may be shown in the display 350.

The clinician can focus attention on the activation map locations 358 and 362 that are in close proximity to the ablation guidance line 354 that is associated with a resetting of a tachycardia circuit. As described above, a potential ablation site may be confirmed by sensing the evoked response at the potential site using an ablation electrode (or mapping electrode) placed at the site and measuring the actual transit time of an IMD pace electrode pulse to the potential site. If the measured TT approximately matches the stored TT for a VT episode cluster being targeted for treatment, the ablation site is confirmed.

A VT episode that is hemodynamically unstable may be considered "unmappable". Using the activation guidance line 354, a VT previously considered unmappable may be mapped by focusing only on a narrow region corresponding to the guidance line 354 to quickly obtain a regionalized activation map allowing early termination of the induced VT.

In some embodiments, one or more additional ventricular pace electrodes may be used to deliver pacing pulses for measuring TT during a repeated episode of the same type, or sequentially or simultaneously during the same episode, to estimate the distance to the VT circuit from a different pace pulse delivery location. In this case, a second electrode location may be displayed with a corresponding second ablation guidance line. An intersection or common region defined by the two (or more) guidance lines may aid in better localizing of the VT circuit.

Figure 7:
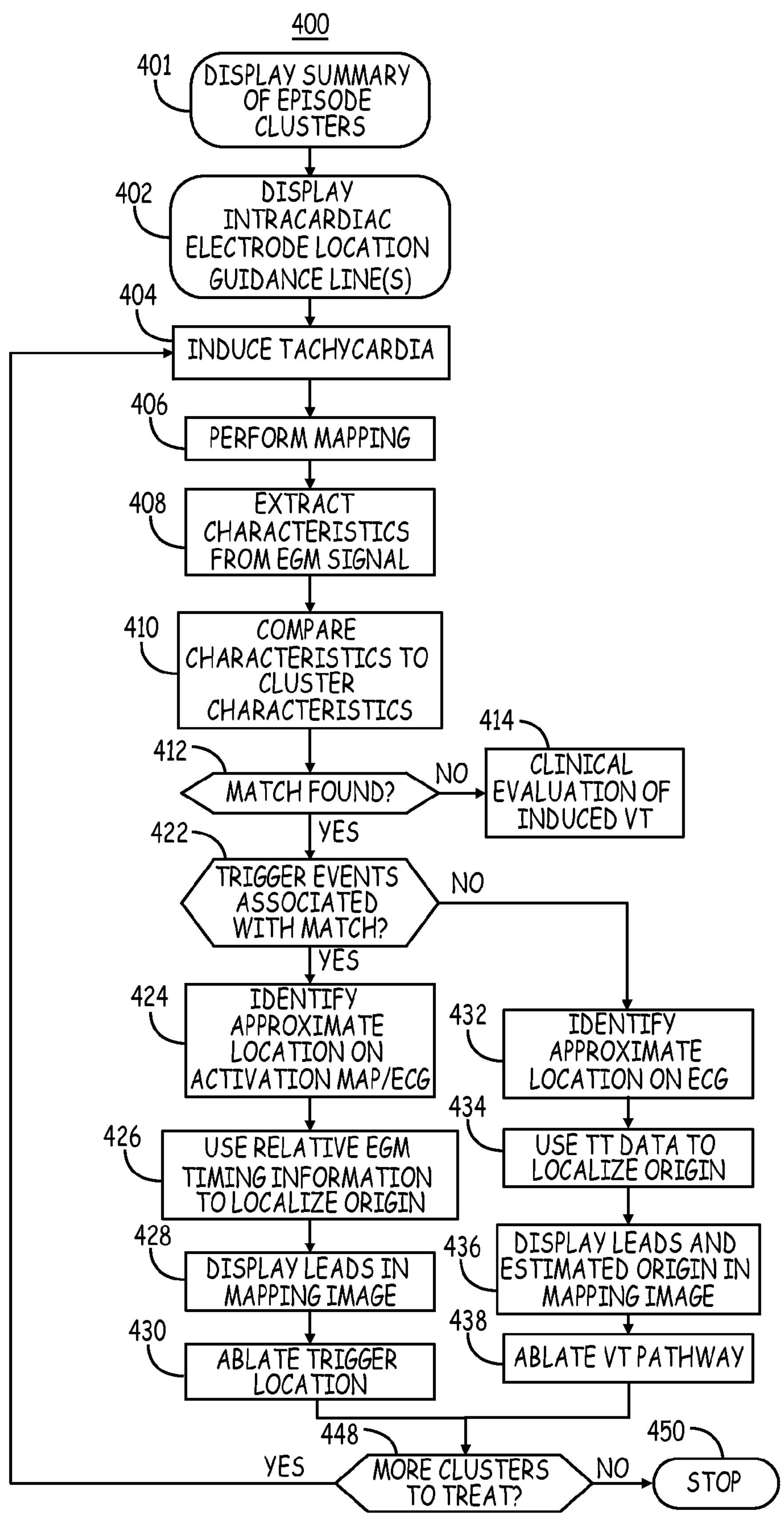
FIG. 7 is a flowchart of a method for using IMD acquired data and an ablation system to localize an ablation site

FIG. 7 is a flowchart 400 of a method for using IMD acquired data and an ablation system in delivering an ablation therapy. It is understood that the various blocks shown in FIG. 7 and in other flowcharts described herein may be arranged in other orders than the order shown and some blocks may be optional or omitted. At block 401, a summary of episode cluster data accumulated by the IMD is displayed, either on an external patient management system 40 or ablation system 42. This summary may include a listing of the number of episode types according to episode cluster data and may be ordered according to frequency of occurrence, potential severity (e.g. TCL or hemodynamic instability), number of delivered therapies by the IMD and associated success rate, or other hierarchical ranking. The clinician may select an episode cluster in the list to review more detailed data about a particular episode type.

At block 402, an image representing the patient's heart is displayed. The location of intracardiac pace electrode(s) used to measure a TT (or RCL) for one or more associated episode clusters is also shown in the display. When TT data is available for an episode cluster, an ablation guidance line is also displayed relative to the associated pace electrode, as generally described in conjunction with FIG. 6. In some cases, ablation at a single site may treat more than one type of VT episode. Simultaneous display of multiple guidance lines may enable a clinician to identify a potential ablation site that may reduce more than one type of VT episode simultaneously.

At block 404, tachycardia is induced to confirm diagnosis and indication of ablation therapy for an inducible VT episode. At block 406 mapping is performed. If an induced VT is hemodynamically stable and tolerated by the patient, mapping may be performed during the VT. If not, substrate mapping of the ventricle(s) is performed at block 406. Mapping procedures and preferences will vary between clinical centers. The clinician will have the episode cluster data from the IMD available and be aware of the number of different episode types potentially targeted for treatment by ablation during the mapping procedure. The mapping procedure may variously involve delivering electrical pulses to the patient's heart for inducing tachycardia, performing pace mapping, entrainment mapping, and/or studying surface ECG signals at blocks 404 and 406. Using relative timing differences from EGM signals, RCL, TT or other information, the clinician will have an initial indication of an approximate location of a triggering event site or a tachycardia circuit site. The clinician may use this knowledge in keying in on the activation time and electrogram signals of particular anatomical areas.

The mapping procedure may be performed in a cooperative manner between the IMD system and the ablation system. The IMD system may remain programmed to detect an induced arrhythmia and extract parameters for identifying a matching cluster of episode data. The IMD system may additionally be enabled to initiate an ATP sequence for measuring RCL and TT if reset is detected.

During mapping at block 406, intracardiac EGM signals obtained by the IMD may also be recorded and analyzed. One or more EGM sensing vectors may be sensed to allow differential timing information to be gathered. At block 408, characteristics used to cluster episode data are extracted from the EGM signal(s). For example, a representative morphology, cycle length, slew rate, or other features may be determined. These characteristics are compared to corresponding characteristics of stored episode clusters at block 410 to determine if the clinician has induced a tachycardia that correlates to an episode cluster. If a matching cluster is found, the clinician has identified a VT that corresponds to a VT episode cluster identified by the IMD. If no match is found, the induced VT is evaluated clinically by the physician at block 414 according to individual practice.

If a match if found, a decision is made at block 422 if the currently measured EGM characteristics correlate to trigger events stored in the episode cluster data. For example, the morphology of the mapped signals may correspond to the morphology of a VT cluster associated with a PVC or non-sustained VT identified as a triggering event for a sustained VT cluster. In this case, the location of the triggering event origin may be approximated using the 12-lead ECG signals or other mapping methods. Relative timing information between two or more EGM vectors may be used to further localize the triggering event origin. In a display, the location of the EGM leads and the estimated location of the triggering event origin may be shown at block 428. With this information, the clinician can identify and ablate the triggering event origin at block 430.

If there are no more episode clusters identified by the IMD for treatment, as determined at block 448, the process is stopped at block 450. Ongoing episode cluster data will provide information as to whether the targeted cluster of episodes has been successfully treated or not.

If an associated triggering event is not identified, the matching cluster identified at block 412 may be used to identify the tachycardia site of origin using both mapping data and IMD cluster data at blocks 432 and 434. A clinician will often have a general idea of a location of a tachycardia site of origin, either focal or reentrant forms of tachycardia, through observation of the 12-lead ECG signals or using other mapping methods. The cluster data provides the clinician with additional information for more precisely localizing a site of origin, for example using the TT data at block 434, as described above.

After matching a mapped signal morphology with a stored episode cluster, the TT data stored for the matching cluster is retrieved at block 434 and used to display an approximate distance of the resetting circuit from a pacing electrode on the ablation image at block 436. In this way, matching morphology or timing characteristics are used to identify a matching episode cluster and then stored RCL and TT data for the matching episode cluster are used directly for indicating a site of origin without performing additional RCL or TT measurements during the mapping procedure. It is recognized that in other embodiments, the RCL and TT measurements may be repeated during the mapping study to verify a match between a stored episode cluster and the induced VT or to confirm an ablation electrode location based on a measured TT as described in conjunction with FIG. 5.

The EGM lead/electrode locations and estimated site of origin based on cluster data, e.g. an ablation guidance line based on a TT measurement as described above, can be displayed in the mapped image at block 436 to guide the clinician in ablating the tachycardia origin or pathway at block 438. If there are more stored episode clusters identified by the IMD for potential ablation therapy as determined at block 448, the process returns to block 404 to continue the induction and mapping procedures. If not the process is terminated at block 450. Ongoing episode cluster data acquisition by the IMD will provide evidence of the degree of success of the ablation procedure.

Thus, a system and associated method for guiding ablation therapy have been presented in the foregoing description with reference to specific embodiments. It is appreciated that various modifications to the referenced embodiments may be made without departing from the scope of the invention as set forth in the following claims.

We claim:

1. A medical device system for guiding a cardiac ablation therapy, comprising;

a plurality of implantable electrodes for sensing cardiac signals;

an implantable cardiac event detector coupled to the plurality of implantable electrodes for detecting spontaneous cardiac events from the sensed cardiac signal;

an implantable pulse generator coupled to the plurality of implantable electrodes for delivering pacing pulses;

an implantable controller to control the implantable pulse generator to deliver a plurality of pacing pulses in response to detecting a spontaneous cardiac event using a first electrode of the plurality of implantable electrodes and measure a return cycle length in response to the plurality of pacing pulses;

a processor configured:

to cluster the spontaneous cardiac event with at least one previously detected cardiac event to produce a cluster of spontaneous cardiac events in response to the measured return cycle length; and estimate an ablation site for the cluster of spontaneous cardiac events based on the return cycle length;

an external display configured to display data comprising the estimated ablation site corresponding to the cluster of spontaneous cardiac events to guide the ablation therapy; and an ablation system, the ablation system comprising:

a cardiac electrophysiology mapping system configured to produce electrophysiology mapping results;

an ablation electrode; and an ablation source coupled to the ablation electrode, wherein the display displays the estimated ablation site superimposed with the electrophysiology mapping results produced by the cardiac electrophysiology mapping system, wherein the ablation system, the implantable controller, and the processor are further configured to cooperatively:

induce a tachycardia, determine a characteristic of the induced tachycardia, compare the characteristic of the induced tachycardia to a characteristic of the cluster of spontaneous cardiac events determine if the induced tachycardia matches the cluster of spontaneous cardiac events in response to the comparison, and identify the estimated ablation site as a targeted ablation site in response to the induced tachycardia matching cluster of spontaneous cardiac events.

2. The system of claim 1, wherein the processor is further configured to determine a plurality of characteristics of the spontaneous cardiac event and wherein clustering the spontaneous cardiac event with the at least one previously detected cardiac event further comprises comparing the plurality of characteristics with corresponding characteristics of the at least one previously detected cardiac event.

3. The system of claim 2, wherein the plurality of characteristics of the spontaneous cardiac events comprises a triggering event.

4. The system claim 1, wherein displaying the estimated ablation site comprises displaying a location of the first electrode.

5. The system of claim 4, wherein displaying the estimated ablation site comprises displaying an ablation guidance line located a distance from the first electrode location, the distance computed using the measured return cycle length.

6. A medical device system for guiding a cardiac ablation therapy, comprising:

a plurality of implantable electrodes for sensing cardiac signals;

an implantable cardiac event detector coupled to the plurality of implantable electrodes for detecting spontaneous cardiac episodes from the sensed cardiac signals;

an implantable pulse generator coupled to the plurality of implantable electrodes for delivering pacing pulses;

an implantable controller to control the implantable pulse generator to deliver a plurality of pacing pulses in response to detecting a spontaneous cardiac event using a first electrode of the plurality of implantable electrodes and measure a return cycle length in response to the plurality of pacing pulses;

a processor configured to cluster the spontaneous cardiac event with at least one previously detected cardiac event to produce a cluster of spontaneous cardiac events in response to the measured return cycle length;

the processor further configured to estimate a targeted ablation site for the cluster of spontaneous cardiac events in response to the measured return cycle length; and an external display configured to display a location of the first electrode and an ablation guidance line located a distance from the displayed first electrode location, the distance computed using the measured return cycle length, wherein the distance corresponds to a minimum distance from the first electrode location to an estimated ablation site for treating the cluster of spontaneous cardiac events.

7. The system of claim 5, wherein the implantable controller is further configured to control the implantable pulse generator to deliver a second plurality of pacing pulses in response to detecting the spontaneous cardiac event using a second electrode of the plurality of implantable electrodes different than the first electrode and measure a second return cycle length in response to the second plurality of pacing pulses, the external display further configured to display a location of the second electrode and a second ablation guidance line located a distance from the second electrode and computed using the second return cycle length.

8. The system of claim 1, wherein the processor is configured to generate an alert when the cluster of spontaneous cardiac events reaches an alert threshold indicating ablation therapy.

9. The system of claim 1, further comprising a communication system coupled to a network for transferring data corresponding to the cluster of spontaneous cardiac events in an electronic format to a data destination.

10. The system of claim 1, wherein the processor is further configured to acquire evidence of success of ablation at the targeted ablation site by determining and comparing a characteristic of a next spontaneous cardiac event to the characteristic of the cluster of spontaneous cardiac events.

11. A medical device system, comprising;

a plurality of implantable electrodes for sensing cardiac signals;

an implantable cardiac event detector coupled to the plurality of implantable electrodes for detecting spontaneous cardiac events from the sensed cardiac signal;

an implantable pulse generator coupled to the plurality of implantable electrodes for delivering pacing pulses;

a control processor configured to:

control the implantable pulse generator to deliver a plurality of pacing pulses in response to detecting a spontaneous cardiac event using a first electrode of the plurality of implantable electrodes;

measure a return cycle length in response to the plurality of pacing pulses;

cluster the spontaneous cardiac event with at least one previously detected cardiac event to produce a cluster of spontaneous cardiac events in response to the measured return cycle length;

estimate an ablation site for the cluster of spontaneous cardiac events based on the return cycle length;

detect an induced tachycardia;

determine a characteristic of the induced tachycardia, compare the characteristic of the induced tachycardia to a characteristic of the cluster of spontaneous cardiac events, determine if the induced tachycardia matches the cluster of spontaneous cardiac events in response to the comparison, and identify the estimated ablation site as a targeted ablation site in response to the induced tachycardia matching the cluster of spontaneous cardiac events.

* * * * *